United States Patent [19]

Smith

[11] Patent Number: 5,328,939

[45] Date of Patent: Jul. 12, 1994

[54] RIGID MATERIALS HAVING HIGH SURFACE AREA AND LOW DENSITY

[75] Inventor: Tammy Smith, Belle Mead, N.J.

[73] Assignee: AlliedSignal Inc., Morris Township, Morris County, N.J.

[21] Appl. No.: 54,114

[22] Filed: Apr. 27, 1993

[51] Int. Cl.$^5$ ............................................ C08B 37/08
[52] U.S. Cl. .................. 521/187; 521/109.1; 521/186; 536/20
[58] Field of Search ............... 521/186, 187, 109.1; 536/20

[56] References Cited

U.S. PATENT DOCUMENTS

| | | | |
|---|---|---|---|
| 4,125,708 | 11/1978 | Masri et al. | 536/20 |
| 4,336,070 | 6/1989 | Koshugi | 106/122 |
| 4,833,237 | 5/1989 | Kawamura et al. | 536/20 |
| 4,879,340 | 11/1989 | Moriguchi et al. | 536/20 |

FOREIGN PATENT DOCUMENTS 56-16532  2/1981  Japan .
58-57401  4/1983  Japan .

*Primary Examiner*—Morton Foelak
*Attorney, Agent, or Firm*—Melanie L. Brown; Gerhard H. Fuchs; Roger H. Criss

[57] ABSTRACT

This invention relates to highly porous, crosslinked bodies derived from nitrogen-containing polymers, and a process of producing the porous bodies which comprises dissolving a nitrogen-containing polymer to form a gel, ionically crosslinking the gel, and covalently further crosslinking the ionically crosslinked gel body.

7 Claims, 1 Drawing Sheet

RIGID MATERIALS HAVING HIGH SURFACE AREA AND LOW DENSITY

BACKGROUND OF THE INVENTION

1. Field of the Invention

The present invention relates to high strength, low density porous bodies derived from nitrogen-containing polymers.

2. Description of the Prior Art

Nitrogen-containing hydrogel polymers, especially chitin and chitosan, have been utilized for many different uses, exploiting their good surface activity and chemical reactivity of the polymers. Chitin is a polysaccharide of poly-N-acetyl-D-glucosamine, which is a constituent material of the outer shells of crustacea, such as shrimp and crab. Chitin is a highly crystalline substance and the intermolecular bonding by its aminoacetyl groups makes the material extremely stable, making chitin highly resistant to solubilization in a wide range of different solvents. Consequently, chitin has been modified a number of different ways to make it soluble and processable. One of such more easily processable derivatives of chitin is chitosan. Chitosan is deacylated chitin and is obtained by heating chitin with concentrated alkali. Chitosan is moderately soluble in water and is easily solubilized in dilute acidic solutions.

There exist many prior art references that disclose different applications utilizing nitrogen-containing polymers, especially chitin and chitosan. Such references include Japanese Patent Specification (Kokai) No. 58-57401, 1983; U.S. Pat. No. 4,125,708 to Masri et al. and U.S. Pat. No. 4,833,237 to Kawamura et al. Kokai No. 58-57401 discloses a process for making porous, granular chitosan bodies that are suitable for such use as chromatographic gels, catalyst carriers and enzyme fixing agents. The process consists of pouring an acidic solution of chitosan and an emulsifier into an aqueous alkali solution while stirring the alkali solution to coagulate and form granular, porous chitosan bodies. However, the resulting granular, porous bodies have a gel-like structure that collapses upon dehydration and has a poor mechanical strength.

Masri et al. discloses sulfite, sulfate, or chloride anion modified chitosan particles that bind superoxy-anion-forming metals, such as chromium, antimony and manganese. The modification process disclosed therein does not involve the steps of dissolving and re-solidifying the dissolved chitosan to form porous bodies, but consists of contacting chitosan particles with an aqueous solution of an appropriate modifying agent such as an acidic form of the above-mentioned anions or salts thereof to produce a compact material. Masri et al. also discloses that the anionically-modified chitosan may be subjected to an additional crosslinking modification, which may be accomplished with a crosslinking reagent, such as glyoxal, glutaraldehyde or dialdehyde starch, before or after the chitosan particles are anionically modified. The modified chitosan, particles of Masri et al. are non-porous particles having a small surface area, making it unsuitable for uses, such as, in high-throughput chromatography applications.

Kawamura et al. discloses a process for producing crosslinked porous chitosan bodies using a low molecular weight chitosan. The process disclosed by Kawamura et al. comprises dissolving a chitosan in an acid, pouring the chitosan solution into a basic solution to precipitate porous chitosan granules, transferring the chitosan granules to a polar solvent, and reacting the chitosan granules with an organic diisocyanate in a polar solvent. The crosslinked porous bodies provide improved strength and porosity. However, the crosslinking process disclosed in the patent subjects the porous bodies to go through a solvent exchange process, in which the porous bodies are exposed to an abrupt change from an aqueous solvent to a polar solvent. This solvent exchange process not only causes portions of the pores to collapse, but also requires additional manufacturing steps that accompanies the solvent exchange process. The collapse of the pores causes the resulting porous bodies to contain uncrosslinked portions that adversely affect dimensional stability of the porous bodies, allowing the porous bodies to shrink and swell upon exposures to different solvents.

SUMMARY OF THE INVENTION

There is provided in accordance with the present invention high-strength, highly porous bodies which are derived from nitrogen-containing polymers, and a process for producing the same. The porous body of the present invention comprises a nitrogen-containing polymer crosslinked with an anionic salt solution and further crosslinked with a covalent-crosslinking agent selected from the group consisting of dialdehydes, aromatic dihalides, formaldehyde, epichlorohydrin, imididates, disulfonyl chlorides, diacid halides, aliphatic dihalides, bisepoxides, diesters, diazides, carbodiimides, aromatic and aliphatic diisocyanates, aromatic and aliphatic diisothiocyanates, bis-azido compounds, 1-fluoro-2-nitro-4-azidobenzene, p-azidophenacyl bromide, N-(azidonitrophenyl)-γ- aminobutyrate hydroxysuccinimide ester, genipin, butene-3,4-oxide, pentafluorobenzaldehyde, chlorobenzaldehyde, fluorobenzaldehyde and mixtures thereof, wherein said porous body has an apparent bulk density of equal to or less than about 0.6 g/cm$^3$ and a surface area of at least 5 m$^2$/g.

The porous bodies of the present invention are produced by a process which comprises dissolving a nitrogen-containing polymer in water or an aqueous acid solution, contacting the dissolved polymer solution to an anionic salt solution to form ionically crosslinked bodies, and contacting the ionically crosslinked bodies to a covalent crosslinking agent to further crosslink covalently.

The porous bodies of the present invention exhibit high porosity and low density as well as high mechanical strength and dimensional stability, making the porous bodies to be suitable materials for use as chromatographic support, resins for biomolecule separation columns, fillers, absorbents, adsorbents, filters, membranes, insulation materials and the like.

DESCRIPTION OF THE DRAWINGS

FIG. 1 depicts a section of the open-celled 3-dimensional lattice of a porous body of this invention. The porous body 10 has pores 11, which form a continuous network of pores.

DETAILED DESCRIPTION OF THE INVENTION

Figure 1:
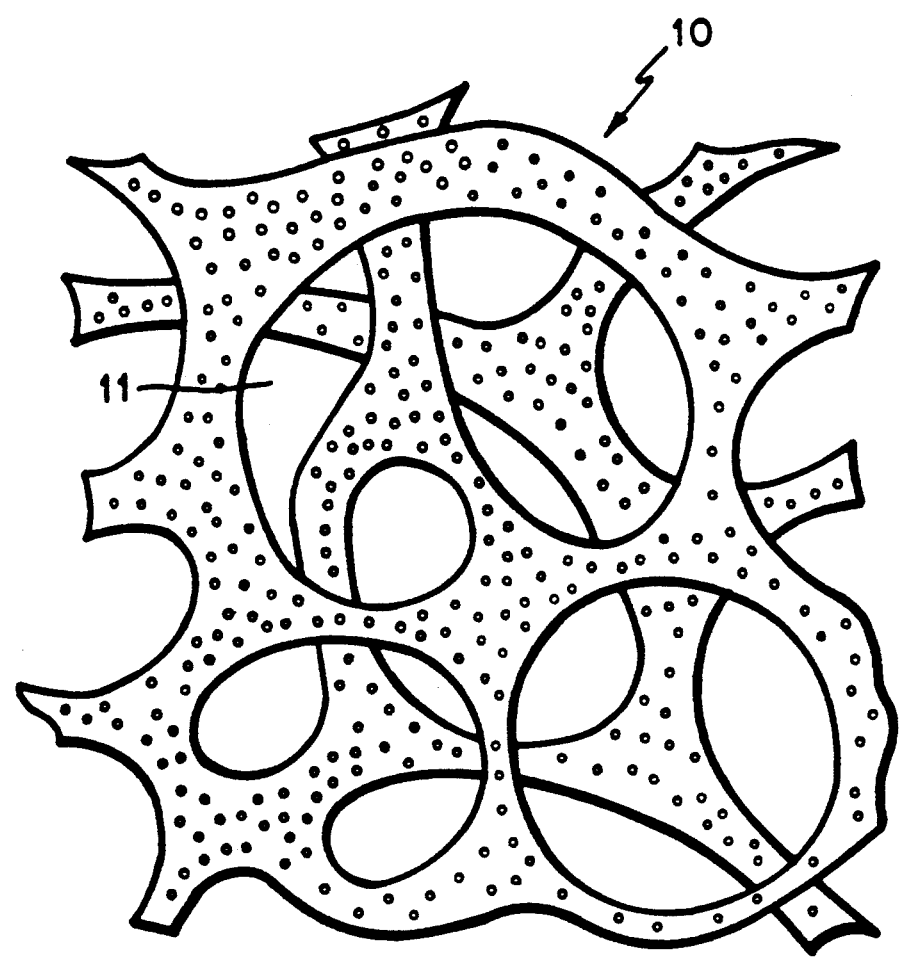
FIG. 1 is a schematic drawing which depicts a porous body of this invention and its open-celled 3-dimensional lattice structure.

The present invention provides highly porous bodies derived from nitrogen-containing hydrogel polymers.

The porous bodies have a high surface area and low density, and exhibit high physical strength. The present invention also provides a process for producing the porous bodies. The term "hydrogel polymer" as used herein indicates a polymer that absorbs water to form a gel-like substance. The present porous bodies are produced by a process which comprises gelling a nitrogen-containing polymer, ionically crosslinking a nitrogen-containing hydrogel polymer with an ionic crosslinking agent, and further crosslinking the ionically crosslinked body with a covalent crosslinking agent.

The present porous bodies are characterized in that they have an apparent bulk density of equal to or less than about 0.6 g/cm$^3$, preferably equal to or less than about 0.5 g/cm$^3$, more preferably equal to or less than about 0.45 g/cm$^3$, and most preferably equal to or less than about 0.4 g/cm$^3$. Additionally, the present porous bodies have a unit surface area of at least about 5 m$^2$/g, preferably at least about 10 m$^2$/g, more preferably 30 m$^2$/g, and most preferably about 90 m$^2$/g.

Although it is not wished to be bound by any theory, it is believed that the advantageous properties of the present porous bodies derive from the formation of the ionic bonds, which crosslink the amine groups of the nitrogen-containing polymers of the present invention, and the formation of the covalent bonds, which further crosslink the amine groups as well as other functional groups, such as the hydroxyl groups, that are present in the nitrogen-containing polymers. The combination crosslinkages of the ionic and covalent bonds render the present bodies to have a high physical strength even though they are highly porous.

In accordance with the present invention, any nitrogen-containing hydrogel polymers can be employed for the present invention. Suitable nitrogen-containing hydrogel polymers include natural and synthetic nitrogen-containing polymers such as chitosan, poly(amino-styrene), poly(vinylpyridine), poly(diaminodiphenylmethane), poly (aminoaniline), poly(ethylenimine), poly(vinylpyrrolidone) and the like, as well as mixtures thereof. Of these suitable polymers, the most preferred is chitosan. Chitosan, as stated above, is prepared by hydrolyrically deacylating chitin. The suitable chitosan for the present invention has a degree of deacylation of at least about 50%, preferably at least about 75%, and more preferably at least about 80%.

In accordance with the present invention, the nitrogen-containing hydrogel polymers are dissolved in water or an aqueous solution of an acidifying agent at a pH between about 7.0 and about 2.0, preferably at a pH of from about 6.9 to about 3.0, to form a polymer solution to form gels. Suitable acidifying agents for use herein include any Brönsted acids, i.e. acids that act as a source of protons, such as acetic acid, adipic acid, formic acid, lactic acid, propionic acid, malic acid, succinic acid, pyruvic acid, hydrochloric acid, nitric acid, phosphoric acid and the like, as well as mixtures thereof. Of these, preferred are organic acids, for example, acetic acid, adipic acid, formic acid, lactic acid, propionic acid, malic acid, succinic acid, pyruvic acid and the like. Most preferred is acetic acid.

The suitable concentration of the nitrogen-containing hydrogel polymer can be varied in accordance with varying needs of different applications. The starting hydrogel concentration has been found to be directly related to the density of resulting crosslinked, porous bodies; the higher the hydrogel polymer concentration, the more dense the porous bodies become. However, the starting hydrogel polymer concentration should be between the minimum concentration sufficient enough to form a gel and the maximum concentration just below the saturation point of the selected polymer. The preferred concentration of the nitrogen-containing polymers is between about 0.02 to about 25 wt %, more preferred is about 0.1 to about 20 wt %, and most preferred is between about 1 to about 15 wt %.

The nitrogen-containing hydrogel polymer solution is gelled and then ionically crosslinked by contacting it with an aqueous solution of an anionic salt. Illustrative of the suitable anionic salts are salts of sulfate, phosphate, polyphosphate, tripolyphosphate, o-benzaldehyde sulfonate, pyrophosphate, trimetaphosphate and the like, as well as mixtures thereof. The suitable salt-forming ions for the present anionic salts are ammonium, bnium and metals of Groups IA, IB, IIA, IIB, IIIA and VIII of the periodic table, such as Na, K, Cu, Mg, Ca, Ba, Zn, Cd, Al, Fe, Co and Ni, and the like. Illustrative examples of the suitable anionic salts for use herein are disodium pyrophosphate, trisodium trimetaphosphate, penta sodium tripolyphosphate, stannous pyrophosphate, tributyl-ammonium pyrophosphate, sodium phosphate glasses, phosphate glasses, e.g., polyphosphate, sodium hexametaphosphate and sodium septaphosphate, ferric pyrophosphate, sodium salts of benzaldehyde sulfonic acid, polyphosphoric acid or adipic acid, sodium sulfate, sodium phosphate dibasic, sodium dodecyl sulfate and the like, as well as mixtures thereof. Of these, the preferred are disodium pyrophosphate, trisodium trimetaphosphate, pentasodium tripolyphosphate, sodium salt of benzaldehyde sulfonic acid, sodium phosphate glasses and phosphate glasses. The most preferred is sodium salt of tripolyphosphate. The suitable concentration of the ionic crosslinking agent for the present invention is in the range of about 0.01 molar to about 2 molar, preferably about 0.05 molar to about 1 molar, more preferably about 0.075 molar to about 0.7 molar, and most preferably about 0.1 molar to about 0.4 molar.

The ionic crosslinking procedure of the present invention can be carried out at any temperature in which the nitrogen-containing hydrogel polymer solution does not freeze or rapidly evaporate. The preferred temperature range is between about 0° C. and about 300° C., and more preferably, between about 20° C. and about 100° C. If a temperature higher than or near the boiling point of water is used, a pressure higher than one atmospheric pressure should be applied in order to prevent rapid evaporation of the crosslinking solvent and the crosslinking agent.

The nitrogen-containing hydrogel polymer solution may be shaped into any desirable form, including sheets, fibers and granules, in accordance with the needs of particular applications. For example, the nitrogen-containing hydrogel polymer solution can be sprayed or dripped into the anionic salt solution to form granular or spherical particles of crosslinked porous bodies.

In accordance with the present invention, the ionically crosslinked bodies are further crosslinked with a covalent crosslinking agent to provide added strength and dimensional stability to the resulting crosslinked porous bodies. Suitable covalent crosslinking agents are any crosslinking agent known in the art to form covalent bonds, including, but not limited to, dialdehydes, e.g., glutaraldehyde, glyoxal, piperazine dicarboxaldehyde, succinic aldehyde, adipic aidehyde, and maleic aldehyde; aromatic dihalides, e.g., 1,3-difluoro-2,4-dinitrobenzene, 1,5-difluoro-2,4-dinitro-benzene, and p,p'-difluoro m,m-dinitrodiphenylsulfone; formaldehyde; epichlorohydrin; imididates, e.g., dimethylsuberimidate, ethyl chloroacetimidate, and poly-methylene diimidates; disulfonyl chlorides, e.g., α-naphthol -2,4-disulfonyl chloride, and phenol-2,4-disulfonyl chloride; diacid halides, e.g., phosgene and dibromophosgene; aliphatic dihalides, e.g., 1,3-dibromoacetone; bismaleimides, e.g., N,N'-phenylene dimaleimides; bisepoxides, e.g., 1,3-bis-(2,3-epoxypropoxy)butane, diepoxybutane and ethyleneglycol diglycidyl ether; diesters, e.g., adipate bis-(p-nitrophenyl ester), carbonyl bis(methionine p-nitrophenyl ester) bishydroxysuccinimide succinate, N-(azidonitrophenyl)-γ-aminobutyrate hydroxy-succinimide ester, bis-tert-butyl-oxylcarbonyl-2,7-diaminosuberic acid bis-2,4,5-trichlorophenyl ester, and dimethyl adipimidate; diazides, e.g., tartaryl diazide, tartaryl bis(glycylazide), and N,N'-bis(p-azido-o-nitrophenyl) 1,3 diamino-2-propanol; carbodiimides, e.g., 1-ethyl-3-(3-dimethylaminepropyl) carbodiimide; aromatic diisocyanates, e.g., tolylene 2,4odiisocyanate, and tolylene 2,6-diisocyanate; aromatic diisothiocyanates, e.g., tolylene diisothiocyanate, and m-phenylene diisothiocyanate; aliphatic diisocyanates, e.g., hexamethylene diisocyanate; aliphatic diisothiocyanates, e.g., hexamethylene diisothiocyanate; aromatic bis-azido compounds; haloketones, e.g., 1,3-dibromoacetone; compounds having mixed functionalities, e.g., 1-fluoro-2-nitro-4-azidobenzene, p-azidophenacyl bromide, pentafluorobenzaldehyde, chlorobenzaldehyde, fluorobenzaldehyde, N-(azidonitrophenyl)-γ-aminobutyrate hydroxysuccinimide ester, genipin, and butene-3,4-oxide; and mixtures thereof. Of these, preferred are dialdehydes, glutaraldehyde, glyoxal, succinic aidehyde, adipic aidehyde, and maleic aidehyde, and the most preferred are glutaraldehyde and glyoxal. The covalent crosslinking agents can be directly added to the ionic salt solution in which the nitrogen-containing polymer was ionically crosslinked. Alternatively, the crosslinking solvent containing the ionic crosslinking agent may be decanted and washed off before the covalent crosslinking agent is applied to the ionically crosslinked bodies.

The covalent crosslinking procedure can be carried out at any temperature in which the solvent containing the ionically crosslinked gel and the covalent crosslinking agent do not freeze or rapidly evaporate. It has been found that increasing the crosslinking temperature increases the speed of the crosslinking reaction. Consequently, the covalent crosslinking procedure is preferably conducted near the boiling point of the solution of the crosslinking agent in a device equipped with a refluxing apparatus to minimize the evaporation of the crosslinking solvent and the agent.

Unlike the prior art crosslinking processes as disclosed, for example, in U.S. Pat. No. 4,833,237, the present process does not employ different solvents for the gelling and crosslinking steps, thereby eliminating the prior art problem of collapsing the gel pores and shrinking the gelled, pre-crosslinked porous bodies when the gelling solvent is exchanged with a crosslinking solvent. It has been found that the collapsed pores resulting from the prior art crosslinking procedures prevent the crosslinking agent from having access to the pores, making the resulting porous bodies to contain uncrosslinked portions. Such uncrosslinked portions are free to swell and shrink, rendering the porous bodies to be dimensionally unstable. In contrast, the porous bodies of the present invention are evenly and thoroughly crosslinked, and thus exhibit high dimensional stability.

The extent of crosslinkage of the present porous bodies can be varied to suit varying needs of different uses of the present porous bodies. The novel crosslinking process of the present invention that does not promote the collapse of the gel pores can facilitate up to 100% crosslinkage of all available functional groups present in the porous gels. Since, as is known in the art, the maximum molar concentration of available functionalities can be empirically calculated for a given starting concentration of each nitrogen-containing polymer, the approximate amount of crosslinking agent needed to accomplish a desired level of crosslinkage can easily be determined.

The resulting fully-crosslinked porous bodies are recovered and then solvent-exchanged and/or dehydrated in accordance with any known procedures in the art. The crosslinked porous bodies can be subjected to a solvent exchange process to replace the gelling and crosslinking solvents with an organic or inorganic solvent. Alternatively, the crosslinked porous bodies can directly be subjected to a dehydration process without the solvent exchanging step. Suitable dehydration processes include air drying, and drying within a heated vacuum apparatus at a temperature between about 20° C. and about 100° C. or higher. The drying conditions are selected in order to effect rapid evaporation of unreacted, volatile crosslinking agents and solvents inside the crosslinked porous bodies without collapsing the pores of the porous bodies.

The crosslinked nitrogen-containing hydrogel polymer bodies of the present invention have high mechanical strength, surface area, low apparent bulk density, high porosity, and good chemical and solvent resistance. In addition, the crosslinked nitrogen-containing hydrogel polymer bodies, when highly crosslinked, exhibit low or no swellability when the porous bodies are dehydrated and rehydrated. In addition, since the present process does not require the nitrogen-containing hydrogel polymers to be gelled and than transferred to a different solvent to be crosslinked, the manufacturing process is significantly simplified and does not result in the collapse of the pores or the shrinkage of the gelled bodies, thereby providing evenly crosslinked porous bodies.

The crosslinked porous bodies of the present invention have an open-celled 3-dimensional lattice porous configuration, as illustrated in FIG. 1, and have electrostatically charged, active functionalities throughout the inner and outer surface. These active functionalities can easily be modified with various functional chemicals. In addition, the porous bodies of the present invention are highly porous and have a high unit surface area, making the porous bodies highly suitable for uses as chromatographic support, resins for biomolecule separation columns, fillers, absorbents, adsorbents, filters, membranes, insulation materials and the like.

The following examples are merely illustrative of this invention and should not be considered limiting in any way.

PROCEDURES FOR MEASURING PROPERTIES OF THE MATERIALS

Surface areas were determined by nitrogen adsorption. Samples were first degassed for 16 hours in a helium atmosphere at 50° C. Adsorption/desorption measurements were made on a Quantasorb sorption systems, a continuous flow gas chromatographic instrument, manufactured by Quantachrome Corp., Syosset, N.Y. Values reported are based on single point measurements at liquid nitrogen temperature, 78K, and 0.3 partial pressure of nitrogen in helium with a total flow rate of 20 cm$^3$/min. The surface areas were calculated using the BET (Brunauer, Emmett and Teller) isotherm following the procedure recommended by the equipment manufacturer.

The particle bulk density and average pore diameter were determined by mercury porosimetry. Samples were first degassed for 16 hours in a helium atmosphere at 50° C. Measurements were made on a Autopore 9210 mercury porosimeter manufactured by Micrometerics, Norcross, Ga. Measurements were taken over the pressure range 20 to 60,000 lb/in2 (138,000 to 410,000,000 Pa) at 60 points with roughly equal logarithmical spacing. Pressures are converted to pore diameters via the Washburn equation where the surface tension of mercury, 485 dyne/cm, and the contact angle, 140°, are assumed. The corresponding pore diameters go from 10 μm to 3.6 nm. The particle bulk density is measured at 20 lb/in$^2$ (138,000 Pa), and the apparent bulk density is calculated by measuring the volume of a known weight of packed granules having a size range between about 20 and about 40 mesh. The average pore diameter is defined as four times the ratio of the pore volume to the total pore area, where the pore surface for pores of a given diameter is calculated from the incremental pore volume assuming cylindrical shape. Procedures followed for operation and analysis were those recommended by the manufacturer of the porosimeter.

EXAMPLES

Example 1

15 g of chitosan, Profloc 320, available from Protan, Inc., New Hampshire, was dissolved in 300 ml of an aqueous 0.05 % acetic acid solution. 20g of the chitosan solution were placed into a test tube and 30 ml of 0.2M tripolyphosphate pentasodium salt (tripolyphosphate) solution was added to the test tube. The test tube was undisturbed for eight days to allow the chitosan to be ionically crosslinked. The excess tripolyphosphate was drained to 100 ml, and 40 ml of 20% glutaraldehyde solution was added. The chitosan solution was reacted at room temperature for 3 days. The crosslinked chitosan body was recovered and thoroughly washed with water before air dried. The test results are shown in Table 1.

Example 2

The procedure outlined in Example 1 was repeated, except 30 ml of 0.2M sodium sulfate solution was employed as the ionic crosslinking agent in place of tripolyphosphate. The test results are shown in Table 1.

Example 3

15 g of chitosan, Profloc 320, was dissolved in 300 ml of an aqueous 0.05 % acetic acid solution. 15 g of the chitosan solution were placed into a test tube and 20 ml of 0.2M disodium pyrophosphate was added to the test tube. The test tube was undisturbed for eight days to allow the chitosan to be ionically crosslinked. The excess disodium pyrophosphate was drained, and a thin layer of top skin was removed before 15 ml of 25% glutaraldehyde solution was added. The chitosan solution was undisturbed for 3 days at room temperature. The crosslinked chitosan body was recovered, thoroughly washed with water, and air dried. The results are shown in Table 1.

Example 4

The procedure outlined in Example 3 was repeated except trisodium trimetaphosphate was used as the ionic crosslinking agent. The results are shown in Table 1.

Example 5

5 g of chitosan, Profloc 320, was dissolved in 100 ml of an aqueous 0.1% acetic acid solution, and the chitosan solution was centrifuged to remove trapped air bubbles. 4 g of the chitosan solution were placed into a test tube and 10 ml of 0.2M o-benzaldehyde sulfonic acid, sodium salt, was added to the test tube. The test tube was undisturbed for overnight to allow the chitosan to be ionically crosslinked. The excess ionic crosslinking agent solution was drained, and 10 ml of 25% glutaraldehyde solution was added. The chitosan solution was undisturbed for 2 days at room temperature. The crosslinked chitosan body was recovered, thoroughly washed with water, and air dried. The results are shown in Table 1.

Example 6

15 g of chitosan, Profloc 320, was dissolved in 300 ml of an aqueous 0.05 % acetic acid solution, and the chitosan solution was centrifuged to remove air bubbles. Into the chitosan solution, 300 ml of 0.2M tripolyphosphate was added, and left undisturbed for 14 days to allow the chitosan to ionically crosslink. The resulting crosslinked body was cut into cubes. The cubes were added to 300 ml of 20% glutaraldehyde solution, and left undisturbed for 8 days at room temperature. The glutaraldehyde solution was then drained and replaced with fresh 300 ml of 20% glutaraldehyde, and heated to reflux for 5 hours to accelerate the crosslinking process. The crosslinked chitosan body was recovered, thoroughly washed with water, and air dried. The results are shown in Table 1. Additionally, the physical strength (compressive strength) of the porous body was tested on a Universal Instron Machine using the ASTMD 1621-73 testing procedure, and the result was 144 psi (1.0 MPa).

Example 7

15 g of chitosan, Profloc 320,was dissolved in 300 ml of an aqueous 0.05 % acetic acid solution, and the chitosan solution was centrifuged to remove air bubbles. The chitosan solution was added to 300 ml of 0.2M tripolyphosphate solution in a drop-wise fashion using a syringe in order to produce granular porous bodies, and the granular bodies were left undisturbed for 6 days. Then 300 ml of 20% glutaraldehyde solution was added and undisturbed for 15 days at room temperature. Then the remaining procedures outlined in Example 6 were followed. The results are shown in Table 1.

Example 8

9 g of chitosan Profloc 320 SD, a self-dissolving grade which contains adipic acid, was dissolved in 300 ml of 8.9% acetic acid solution. Then the procedures outlined in Example 7 were repeated. The results are shown in Table 1.

Control 1 (C1)

15 g of chitosan, Profloc 320, was dissolved in 300 ml of an aqueous 0.05% acetic acid solution. The chitosan solution was air dried, resulting in a globular structure of a thin, brittle film. The surface area of the resulting material is shown in Table 1.

Control 2 (C2)

15 g of chitosan, Profloc 320, was dissolved in 300 ml of an aqueous 0.05% acetic acid solution. 20 g of the chitosan solution were placed into a test tube and 30 ml of 0.2M tripolyphosphate was added to the test tube. The test tube was undisturbed for eight days to allow the chitosan to be ionically crosslinked. When the resulting ionically crosslinked chitosan body was air dried, the chitosan body shrank to form a compact material. The surface area and density of the dried chitosan body were measured, and the results are shown in Table 1.

Control 3 (C3)

15 g of chitosan, Profloc 320, was dissolved in 300 ml of an aqueous 0.05% acetic acid solution. 20 g of the chitosan solution were placed into a test tube and 30 ml of 20% glutaraldehyde solution was added to the test tube. The test tube was undisturbed for eight days to allow the chitosan to be covalently crosslinked. When the resulting covalently crosslinked chitosan body was air dried, the chitosan body shrank to form a compact material. The surface area and density of the dried chitosan body were measured, and the results are shown in Table 1.

Control 4 (C4)

A control specimen was prepared by following the procedure outlined in Example 1 (ii) of U.S. Pat. No. 4,125,708. Proflec 320 was ground to pass a 40–60 mesh screen, and 3.0 g of the ground chitosan was mixed with 22.5 millimoles of sodium dithionite and 15 millimoles of acetic acid in 30 ml of water. The mixture was stirred and held at 25° C. for 2 hours. The resulting solids were separated and washed with water (75 ml), methanol (15 ml) and then ethanol (75 ml), and air-dried.

The chitosan in this procedure did not form a gel, but it stayed as a suspension of insoluble solids. The surface area of the resulting particle was measured as shown in Table 1.

TABLE 1

| Example | SA (m²/g) | ABD (g/cm³) | APD (nm) | PA (m²/g) |
|---------|-----------|-------------|----------|-----------|
| 1 | 93 | 0.28 | 51.0 | 124 |
| 2 | 41 | 0.34 | — | — |
| 3 | 50 | 0.31 | — | — |
| 4 | 38 | 0.32 | — | — |
| 5 | 20 | 0.15 | — | — |
| 6 | 94 | — | 141.0 | 84 |
| 7 | 126 | 0.23 | 38.4 | 163 |
| 8 | 37 | 0.39 | — | — |
| C1 | 0.24 | — | — | — |
| C2 | 0.24 | 0.7 | — | — |
| C3 | 0.2 | 1.85* | — | — |
| C4 | 1.5 | — | — | — |

SA = surface area
ABD = apparent bulk density
APD = average pore diameter
PA = pore area
*particle density (g/cm³)

As can be seen from the above results, subjecting a solution of a nitrogen-containing hydrogel polymer with either an ionic crosslinking process or a covalent crosslinking process alone does not provide the porous bodies of the present invention that have a high surface area and physical integrity. In addition, as can be seen from the result of Control 4, unless the nitrogen-containing hydrogel polymer is solubilized and then crosslinked, the resulting crosslinked bodies do not form porous bodies and do not have a high surface area. In contrast, the nitrogen-containing polymer bodies that are produced in accordance with the present invention are highly porous and have a low density as well as high mechanical strength, making the porous bodies to be suitable materials for use as chromatographic support, resins for biomolecule separation columns, fillers, absorbents, adsorbents, filters, membranes, insulation materials and the like.

What is claimed is:

1. A crosslinked porous body comprising a nitrogen-containing polymer crosslinked with an anionic salt solution and further crosslinked with a covalent-crosslinking agent selected from the group consisting of dialdehydes, aromatic dihalides, formaldehyde, epichlorohydrin, imididates, disulfonyl chlorides, diacid halides, aliphatic dihalides, bisepoxides, diesters, diazides, carbodiimides, aromatic and aliphatic diisocyanates, aromatic and aliphatic diisothiocyanates, aromatic bisazido compounds, 1-fluoro-2-nitro-4-azidobenzene, p-azidophenacyl bromide, N-(azidonitrophenyl)-γ-aminobutyrate hydroxysuccinimide ester, genipin, butene-3,4-oxide, pentafluorobenzaldehyde, chlorobenzaldehyde, fluorobenzaldehyde, and mixtures thereof, wherein said porous body has an apparent bulk density of equal to or less than about 0.6 g/cm³ and a surface area of at least 5 m²/g.

2. The crosslinked porous body of claim 1, wherein said nitrogen-containing polymer is selected from the group consisting of chitosan, poly(amino-styrene), poly(vinylpyridine), poly(diaminodiphenyl-methane), poly (aminoaniline), poly(ethylenimine), poly(vinylpyrrolidone) and mixtures thereof.

3. The crosslinked porous body of claim 1, wherein said nitrogen-containing polymer is chitosan.

4. The crosslinked porous body of claim 1, wherein said anionic salt is selected from the consisting of the ammonium, onium and metal salts of sulfate, phosphate, polyphosphate, tripolyphosphate, o-benzaldehyde sulfonate, pyrophosphate, trimetaphosphate and mixtures thereof.

5. The crosslinked porous body of claim 1, wherein said covalent-crosslinking agent is selected from the group consisting of glutaraldehyde, glyoxal, piperazine dicarboxaldehyde, succinic aidehyde, adipic aidehyde, maleic aidehyde, and mixtures thereof.

6. The crosslinked porous body of claim 1, wherein said covalent-crosslinking agent is glutaraldehyde.

7. A crosslinked porous body comprising chitosan crosslinked with a tripolyphosphate solution and further crosslinked with glutaraldehyde, wherein said porous body has an apparent bulk density of equal to or less than about 0.6 g/cm³ and a surface area of at least 5 m²/g.

* * * * *